United States Patent [19]
Aldomá et al.

[11] Patent Number: 5,672,613
[45] Date of Patent: Sep. 30, 1997

[54] 2-(4-METHOXYPHENOXY)-3-PYRIDINEAMINE, ITS PHARMACEUTICAL COMPOSITIONS AND THERAPEUTIC USE

[75] Inventors: Gustavo Enrique Aldomá; Susana Elida Piatti, both of Buenos Aires, Argentina

[73] Assignee: Handforth Investments Ltd., Isle of Man, United Kingdom

[21] Appl. No.: 687,565

[22] PCT Filed: Feb. 13, 1995

[86] PCT No.: PCT/EP95/00525

§ 371 Date: Aug. 9, 1996

§ 102(e) Date: Aug. 9, 1996

[87] PCT Pub. No.: WO95/22528

PCT Pub. Date: Aug. 24, 1995

[30] Foreign Application Priority Data

Feb. 22, 1994 [DE] Germany ............ 44 05 641.9

[51] Int. Cl.⁶ ............ A61K 31/44; C07D 213/72; C07D 213/36
[52] U.S. Cl. ............ 514/348; 546/301; 546/297
[58] Field of Search ............ 546/301, 297; 514/348

[56] References Cited

U.S. PATENT DOCUMENTS

| | | | |
|---|---|---|---|
| 3,840,597 | 10/1974 | Moore et al. | 564/97 |
| 5,104,656 | 4/1992 | Seth et al. | 424/401 |
| 5,210,099 | 5/1993 | Mody et al. | 514/557 |

FOREIGN PATENT DOCUMENTS

| | | |
|---|---|---|
| 0 405 487 A1 | 1/1991 | European Pat. Off. . |
| 0 532 900 A1 | 9/1991 | European Pat. Off. . |
| 2339993 | 2/1974 | Germany . |
| 92/13842 | 1/1992 | WIPO . |

OTHER PUBLICATIONS

J. Invest. Dermat. J. M. Young, Tachyphylaxis in 12–0–Tetradecanoylphorbol Acetate– and Arachidonic Acid–Induced Ear Edema, vol. 80, pp. 48–52, 1983.

Proc. Soc. Ep. Biol. Med, C.A. Winter, et al, vol. III, pp. 544–547, 1962.

*Primary Examiner*—Alan L. Rotman
*Attorney, Agent, or Firm*—St. Onge Steward Johnston & Reens LLC

[57] ABSTRACT

The product 3-amino-2-(4-methoxyphenoxy)pyridine and its pharmaceutically suitable salts, in particular the hydrochloride, are novel products which are prepared by catalytic hydrogenation of 2-(4-methoxyphenoxy)-3-nitropyridine, optionally in the presence of the acid corresponding to the salt. Its pharmaceutical compositions containing sufficient amounts of suitable auxiliaries for its topical administration prove particularly useful in therapy for the treatment of inflammatory skin diseases. The tests for dermatological action with the aid of TPA-induced mouse ear oedema and of carragenan-induced rat paw oedema show that the product is very much more active by the topical route than ibuprofen and nimesulide, two known anti-inflammatory active compounds, of which the first is very widely known and the second structurally related.

6 Claims, No Drawings

2-(4-METHOXYPHENOXY)-3-PYRIDINEAMINE, ITS PHARMACEUTICAL COMPOSITIONS AND THERAPEUTIC USE

This application is a 371 of PCT EP 95/00525 filed Feb. 13, 1995.

The present invention relates to a novel product, 3-2-amino-2-(4-methoxyphenoxy)pyridine, a pharmaceutical composition containing this product, a process for its preparation and its therapeutic use, in particular as an anti-inflammatory active compound to be used topically.

PRIOR ART

Despite the large number of known pharmaceutical active compounds in the therapeutic area associated with inflammatory diseases, research and development of novel products and novel pharmaceutical application forms go on and on. This is in the main because of the fact that the non-steroidal, anti-inflammatory products on oral administration bring with them the problem of side-effects in the gastrointestinal region. If the inflammation is superficial and locally restricted, it is attempted to keep these side-effects as small as possible by the topical administration of the product. Thus e.g. ibuprofen (α-methyl-4-(2-methylpropyl) benzeneacetic acid), one of the most-used, orally administered, non-steroidal anti-inflammatory products, is likewise topically applied (cf. U.S. Pat. No. 5,210,099 or U.S. Pat. No. 5,104,656).

The most related commercially available product to the present invention in its structure is presumably nimesulide or N-(4-nitro-2-phenoxyphenyl)methane-sulphonamide, which was first described in the document U.S. Pat. No. 3,840,597. In this patent, its possible topical application in the form of a cream or of a gel is already mentioned. Its topical application in the form of an ointment is additionally the subject of the more recent patent EP-A-0 532 900.

3-Amino-2-(4-methoxyphenoxy)pyridine, to which the present invention relates, is generally described on page 7 of the Patent Application WO 92/13842 as a theoretical possibility in a general formula of intermediary steps for the preparation of derivatives of the type N-(2-aryloxy-6-nitro) alkylsulphonamide. The preparation of this product and its features, however, are not expressly mentioned either in the said patent or in any other document, which is why it is a chemically novel product.

DESCRIPTION OF THE INVENTION

The object of the present invention is the preparation of 3-amino-2-(4-methoxyphenoxy)pyridine and its pharmaceutically suitable salts, among these particularly preferably the hydrochloride.

Besides 3-amino-2-(4-methoxyphenoxy)pyridine, the present invention additionally relates to pharmaceutical compositions which contain therapeutically active amounts of the product 3-amino-2-(4-methoxyphenoxy)pyridine or of pharmaceutically suitable salts thereof and sufficient amounts of suitable auxiliaries. The preferred auxiliaries are found among those suitable for topical administration, in the form of creams, gels, ointments, unguents, eye drops and the like. The invention likewise includes the use of the product 3-amino-2-(4-methoxyphenoxy)pyridine or a pharmaceutically suitable salt thereof in the production of medicaments for the treatment of inflammatory syndromes.

Although 3-amino-2-(4-methoxyphenoxy)pyridine, to which the present invention relates, can be administered orally, this product is especially preferred for topical application, which is why it has proven particularly suitable for the control of inflammatory skin and eye diseases, such as of allergic or photoallergic dermatitis, contact dermatitis, of sunburn, nettle-rash, eczema, atopic dermatitis, exfoliative dermatitis, psoriasis, etc.

The present invention makes available a preparation process for 3-amino-2-(4-methoxyphenoxy)pyridine, which is characterized in that 2-(4-methoxyphenoxy)-3-nitropyridine is catalytically hydrogenated in a suitable solvent. In a particular embodiment, the catalyst used is palladium on carbon and the solvent is ethyl acetate. The above starting material, 2-(4-methoxyphenoxy)-3-nitropyridine, is preferably obtained by reaction between 2-chloro-3-nitropyridine and the alkali metal salt of 4-methoxyphenol using toluene as a solvent. The pharmaceutically suitable salts of 3-amino-2-(4-methoxyphenoxy)pyridine are prepared by reaction with the corresponding acids either in situ or in consecutive steps. For the preparation of the hydrochloride, the hydrogenation process in the presence of hydrochloric acid in a mixture of ethyl acetate and ethanol is preferred.

The anti-inflammatory action on topical administration of 3-amino-2-(4-methoxyphenoxy)pyridine was compared with that of known anti-inflammatory products whose use by the topical route has been described. To be precise on the one hand using ibuprofen as a classical, widely used product, even if structurally not very similar; and on the other hand using nimesulide as a newer, but structurally related product. Additionally, two standard tests for dermatological action were carried out, to be precise the TPA-induced mouse ear oedema and carragenan-induced rat paw oedema tests. In the first, the inhibitory action of the topically applied product on the oedema produced in the ear of the mouse by an application of 12-O-tetradecanoylphorbol (TPA) acetic acid ester is measured. In the second, the inhibitory action of the topically applied product on the oedema caused by subplantar injection of carragenan in the paw of the rat is measured. The results of these tests, which are listed in Table 1, show that 3-amino-2-(4-methoxy-phenoxy)pyridine has a surprisingly high anti-inflammatory action on topical application, much higher than that of the two reference products, which is a great advantage.

TABLE 1

Anti-inflammatory action on topical application, expressed as the percentage decline in inflammation

| Product | TPA test (1) | Paw oedema test (2) |
|---|---|---|
| Ibuprofen | 16% | 2.0% |
| Nimesulide | 27% | 15% |
| Product of the invention | 32% | 42% |

Product of the invention = 3-amino-2-(4-methoxyphenoxy)pyridine
(1) 250 μg/mouse ear.
(2) 60 mg/rat paw The following Examples are intended to illustrate the invention.

EXAMPLES

Example 1: Preparation of 3-amino-2-(4-methoxyphenoxy)pyridine and its hydrochloride 5.87 g of 4-methoxyphenol were dissolved in 8 ml of methanol; 2.61 g of KOH were added, the whole was stirred for 2 hours, and the solvent was evaporated. The solid obtained was dissolved in 150 ml of anhydrous toluene. With stirring, 5 g of 2-chloro-3-nitropyridine were added at 70°–80° C. in the course of 4 hours under a nitrogen atmosphere. The whole was then stirred at ambient temperature for 2 hours. It was washed with 10% aqueous NaOH and then with plenty of water. The organic phase was treated with active carbon at room temperature for 60 minutes. It was filtered and the filtrate was dried with anhydrous magnesium sulphate. After evaporation of the solvent at low pressure, 7.4 g of 3-amino-2-(4-methoxyphenoxy)pyridine (95% yield) were obtained as a pale yellow solid which melted at 105°–107° C. with decomposition.

6.40 g of the preceding product were dissolved in 160 ml of ethyl acetate; 100 mg of a suspension of palladium on active carbon containing 50% of water were added, which hydrogenated to complete conversion at 35 psi in the course of 90 min. The whole was filtered, and after evaporation of the solvent and subsequent recrystallization in isopropanol 4.42 g (79%) of 3-amino-2-(4-methoxyphenoxy)pyridine were obtained, which had a melting point of 144°–147° C.

By hydrogenation of the above product in a mixture of ethyl acetate and ethanol as a solvent and in the presence of concentrated hydrochloric acid, the hydrochloride of 3-amino-2-(4-methoxyphenoxy)pyridine was obtained as a white solid which melted at 140°–142° C. with decomposition.

Example 2: Comparison Test of the Anti-Inflammatory, Topical Action by the TPA-Induced Ear Oedema Test 1 µg of TPA (12-O-tetradecanoylphorbol acetate) in 20 µl of acetone was administered to the left ear of mice of both sexes of weight 25±5 g. The solution containing 250 µg in each case of the medicament investigated (nimesulide, ibuprofen and 3-amino-2-(4-methoxyphenoxy)pyridine in each case) was given in the right ear. After 6 hours, both ears were cut off and weighed and the percentage weight loss was measured, which on average gave the following values: 27% with nimesulide, 16% with ibuprofen and 32% with 3-amino-2-(4-methoxyphenoxy)pyridine. The procedure was essentially according to the method described by J. M. Young and colleagues (J. Invest. Dermatol. 1983, Vol. 80, pp. 48–52), but the weight and not the size of the ear was measured.

Example 3: Comparison Test of the Anti-Inflammatory, Topical Action by the Carragenan-Induced Paw Oedema Test 600 mg of a gel was applied topically to the right hind paws of Wistar rats of both sexes of weight 150±50 g, containing placebo in the case of the untreated animals and containing 30 g of the medicament investigated (nimesulide, ibuprofen and 3-amino-2-(4-methoxyphenoxy)pyridine in each case) in the case of the others. After 45 minutes, all animals were given 0.05 ml of a 1% strength carragenan solution in physiological saline solution by the subplantar route, again in the right paw. Two hours later, the treatment was repeated to be with the medicament as above. One hour later, the percentage increase in the treated paw compared with the other was determined, both in the untreated animals and in those treated with the medicaments, the percentage weight losses being calculated, which on average appeared to be as follows: 15% with nimesulide, 2% with ibuprofen and 42% with 3-amino-2-(4-methoxyphenoxy)pyridine. The method described by C. A. Winter and colleagues was mainly used (Proc. Soc. Exp. Biol. Med. 1962, Vol. 111, pp. 544–547) with the modifications necessary for percutaneous administration of the medicament. A plethysmometer of the make Ugo Basile, Model 7150, was used.

We claim:
1. 3-Amino-2-(4-methoxyphenoxy)pyridine or a pharmaceutically suitable salt thereof.
2. Hydrochloride of 3-amino-2-(4-methoxyphenoxy)pyridine.
3. Pharmaceutical composition which contains a therapeutically active amount of 3-amino-2-(4-methoxyphenoxy)pyridine or of a pharmaceutically suitable salt thereof, together with a sufficient amount of an auxiliary or of auxiliaries.
4. Pharmaceutical composition according to claim 3, wherein the auxiliary is selected from those customary for topical application.
5. A method of treating a host or subject for an inflammatory disease comprising administering to said host or subject in need thereof with an effective amount of 3-amino-2-(4-methoxyphenoxy)pyridine or a pharmaceutically suitable salt thereof.
6. A method according to claim 5, wherein the inflammatory diseases are of dermatological type, and in that the medicament is topically administered.

* * * * *